US011040177B2

(12) United States Patent
Aggerholm et al.

(10) Patent No.: US 11,040,177 B2
(45) Date of Patent: Jun. 22, 2021

(54) MEDICAL BALLOON WITH INCORPORATED FIBERS

(71) Applicant: Cook Medical Technologies LLC, Bloomington, IN (US)

(72) Inventors: Steen Aggerholm, St. Heddinge (DK); Tue Bödewadt, Solroed Strand (DK); Thomas Lysgaard, Solroed Strand (DK)

(73) Assignee: Cook Medical Technologies LLC, Bloomington, IN (US)

( * ) Notice: Subject to any disclaimer, the term of this patent is extended or adjusted under 35 U.S.C. 154(b) by 327 days.

(21) Appl. No.: 15/881,025

(22) Filed: Jan. 26, 2018

(65) Prior Publication Data

US 2018/0185621 A1 Jul. 5, 2018

Related U.S. Application Data

(60) Continuation of application No. 14/748,907, filed on Jun. 24, 2015, now Pat. No. 9,901,717, which is a (Continued)

(30) Foreign Application Priority Data

Mar. 27, 2012 (GB) ...................................... 1205362

(51) Int. Cl.
*A61M 25/10* (2013.01)
*B29C 49/48* (2006.01)
(Continued)

(52) U.S. Cl.
CPC ........ *A61M 25/1002* (2013.01); *A61M 25/10* (2013.01); *A61M 25/104* (2013.01);
(Continued)

(58) Field of Classification Search
CPC .............. A61M 25/10; A61M 25/1002; A61M 25/1027; A61M 25/1029; A61M 25/1031; A61M 25/104; A61M 2025/1043
See application file for complete search history.

(56) References Cited

U.S. PATENT DOCUMENTS 7,273,471 B1 * 9/2007 Wang ................. A61M 25/1002
604/103.06
2005/0234500 A1 * 10/2005 Chen ..................... A61L 29/049
606/192

(Continued)

OTHER PUBLICATIONS

Rogers, Tony; Everything You Need To Know About Polyethylene (PE); Creative Mechanisms Blog; Sep. 14, 2015. (Year: 2015).*
Polyurethane, Material Properties, 2020. (Year: 2020).*

*Primary Examiner* — Robert A Lynch
(74) *Attorney, Agent, or Firm* — Woodard Emhardt Henry Reeves & Wagner LLP

(57) ABSTRACT

A balloon catheter assembly comprises a balloon having attached to or in its wall one or more filar elements, extending from one end of the balloon to the other. The filar elements are made of a material which is at least as flexible as the material forming the walls of the balloon. In the event of circular burst of the balloon, the filar element(s) prevent disconnection of the material of the balloon into two or more separate pieces. The filar element(s) become attached to or in the material of the balloon wall when the raw material is inflated to the shape of a mold. The filar elements may comprise a natural fiber, a synthetic fiber or a metal wire.

15 Claims, 6 Drawing Sheets

Related U.S. Application Data division of application No. 13/784,072, filed on Mar. 4, 2013, now abandoned.

(51) Int. Cl.
*B29D 22/02* (2006.01)
*B29L 31/00* (2006.01)
*B29C 49/00* (2006.01)

(52) U.S. Cl.
CPC ......... *A61M 25/1029* (2013.01); *B29C 49/48* (2013.01); *B29D 22/02* (2013.01); *A61M 2025/1031* (2013.01); *A61M 2025/1075* (2013.01); *A61M 2025/1084* (2013.01); *B29C 2049/0089* (2013.01); *B29L 2031/7543* (2013.01)

(56) References Cited

U.S. PATENT DOCUMENTS

2006/0129179 A1* 6/2006 Weber ............... A61M 25/0009
606/194
2007/0250101 A1* 10/2007 Horn ................ A61M 25/1029
606/192
2011/0022152 A1* 1/2011 Grandt .................... A61F 2/958
623/1.12

* cited by examiner

MEDICAL BALLOON WITH INCORPORATED FIBERS

CROSS-REFERENCE RELATED APPLICATIONS

This application claims priority to GB application no. 1205362.5, filed Mar. 27, 2012, titled "Medical Balloon with Incorporated Fibers", and Non-Provisional patent application Ser. No. 13/784,072 filed on Mar. 4, 2013, and Non-Provisional patent application Ser. No. 14/748,907 filed on Jun. 24, 2015, the contents of which are incorporated herein by reference.

TECHNICAL FIELD

The present invention relates generally to medical devices and more particularly to a balloon of a balloon catheter. The teachings herein can be used in balloons used for numerous medical applications, including for example angioplasty, scoring or cutting, occlusion, valvuloplasty, to expand implantable medical devices and so on.

BACKGROUND ART

Balloon catheters, which generally comprise a catheter tube with an inflatable balloon at the distal end thereof, are widely used in the medical profession for various endoluminal procedures. One common procedure involving the use of a balloon catheter relates to angioplasty dilation of coronary or other arteries suffering from stenosis (that is, a narrowing of the arterial lumen which restricts blood flow). Other procedures of the types mentioned above are also practiced in the art.

In all balloon catheter procedures there is a risk that the balloon may burst, either during its inflation or during the medical procedure itself. When balloon burst occurs, only parts of the balloon which remain attached to the catheter are easily recoverable from the site of the procedure by the withdrawal of the catheter. Thus, if the balloon bursts in such a way that all the balloon material remains connected in a single piece, and therefore attached to the catheter, then all of the material of the burst balloon is recoverable by withdrawal of the catheter. On the other hand, if the balloon bursts in such a way that the balloon material becomes circumferentially disconnected into two or more separate fragments or pieces, that is suffers a circumferential burst, only fragments or sections of the balloon material which remain attached to the catheter are recoverable by withdrawal of the catheter. Fragments of the balloon which become disconnected from the catheter are not so easily recovered and can require a separate medical procedure to remove them.

Current methods to address the problems resulting from circumferential burst of medical balloons include increasing the thickness of the material used to form the balloon walls and providing complex balloon structures with strengthening sleeves, braiding or meshes. While these approaches may reduce the chance of balloon burst, they are far from ideal solutions. For example, thickening the balloon walls or introducing additional strengthening elements may reduce the flexibility and compressibility of the balloon, leading to an increase in the balloon and introducer profile. This is contrary to the general desire for as small a balloon and introducer profile as possible.

DISCLOSURE OF THE INVENTION

The present invention seeks to provide an improved medical balloon and balloon catheter assembly.

According to an aspect of the present invention, there is provided a balloon catheter assembly including: a catheter; an inflatable balloon having a longitudinal direction and comprising a balloon wall made from at least one balloon material and provided with a body portion, first and second end cones, and first and second neck portions, which neck portions are attached to the catheter; and one or more filar elements formed of at least one filar material attached to or embedded in the balloon wall, wherein the one or more filar elements extend solely in the longitudinal direction of the balloon from the first neck portion to the second neck portion; wherein the one or more filar elements provide a barrier to circumferential tear propagation.

The filar elements provide circumferential strengthening of the balloon along its entire unsupported length, that is along the entire length of the balloon which is not fixed to and thus supported by the catheter. They provide a barrier to stop the propagation of a circumferentially extending tear in the balloon, thereby no prevent or substantially reduce the risk of the balloon tearing into separate and loose components. More specifically, an advantage of this structure is that if a circumferential balloon burst develops, the filar element or elements halt the circumferential propagation of the tear, thus ensuring that the balloon material remains connected in a single piece and remains attached to the catheter. In this way, the entire balloon is readily recoverable from the site of the procedure by withdrawal of the catheter, even after the event of a circumferential burst.

The filar elements extend solely along the longitudinal direction of the balloon, that is there are no filar elements which extend circumferentially around the balloon in annular manner. This allows the balloon to expand radially outwardly without any material constraint from the filar elements. That is to say, there are no filar elements which extend circumferentially around the balloon, in ring or similar format.

In the preferred embodiment, the filar element or elements do not materially affect the flexibility of the balloon. In practice, the filar elements may be as flexible as the balloon wall at least in a longitudinal direction of the balloon. This leads to a structure in which circumferential propagation of a tear in the balloon wall is halted, without any compromise in the ability of the balloon to expand radially outwards, and without the need for an overly complex balloon structure or thickened balloon wall.

The filar elements thus do not materially or measurably alter the performance of the balloon in terms of the functions intended to be performed by the balloon. They exist solely to prevent complications should the balloon burst. In particular, the filar elements have no scoring or abrading effect on a vessel wall.

In an embodiment, the filar element or elements are compressible, that is in a direction transverse to the longitudinal. Such compressibility minimizes the chance of the filar elements affecting the performance of the balloon, particularly in the case where they are positioned on the surface of the balloon wall or only partially embedded therewith.

Preferably, the balloon wall has a thickness of between about 0.005 millimeters and about 0.080 millimeters and, advantageously, the at least one filar element has a diameter of between around 0.01 millimeters and 0.05 millimeters.

The at least one filar element may be completely embedded in the balloon wall, partially embedded in the balloon wall or may even be positioned on the balloon wall, either on the outside of the balloon or on the inside thereof.

The filar element or elements may be single strand structures or may be multi stranded. Advantageously, the at least one filar material comprises natural and/or synthetic fiber. The material may, for instance, comprise as least one of: para-aramid synthetic fiber such as Kevlar, ultra high molecular weight polyethylene such as Dyneema, polytetrafluoroethylene fiber such as Gore-Tex, carbon fiber, cotton and the like.

In a practical embodiment, the filar elements have a linear density (dtex) of between 10 and 60 and are multi filamentary, each having from around 5 to 50 filaments per strand, preferably around 25 filaments. Each filament may have a density of around 0.5 to 2 denier (or similar dtex density).

The filar elements preferably have a tensile strength of between around 4 N to around 20 N. They may have an elongation at break of no more than around 5%.

The filar element(s) are made of a material resistive to breakage and tear and which is preferably significantly stronger than the balloon wall, thereby being strong enough to halt circumferential propagation of a tear in the balloon wall.

In an embodiment, the balloon wall comprises an outer layer of a first material and an inner layer of a second material, wherein a softening or melting temperature of the first material is lower than a softening or melting temperature of the second material.

The filar element or elements are preferably at least partially embedded in the outer layer of the balloon wall.

The filar element or elements preferably extend longitudinally, that is along the longitudinal axis of the balloon, but may extend at an angle to the longitudinal, such as helically. The filar element or elements preferably do not extend transversely around the circumference of the balloon in annular manner.

The size and flexibility of the filar element(s) is advantageously such that the properties of the balloon, for example its ability to be wrapped onto the catheter, its wall thickness and its flexibility, are not materially affected by the provision of the filar element(s) on or in the balloon wall. This is particularly important when the balloon is for use in more delicate applications, such as in smaller and more delicate vessels including for instance cerebral vessels, where the overall thickness of the balloon catheter, when the balloon is wrapped onto the catheter for endoluminal delivery, may be of the order of 1 mm or less.

The filar elements are such that they do not cause interference with or damage to the interior surface of the lumen at the site to which the balloon is deployed. In this regard, the filar elements may be completely embedded in the balloon wall or produce only a minor protrusion which does not cut or score into the vessel wall. The flexibility of the filar elements will also ensure that these do not cut or score the vessel wall.

According to another aspect of the present invention, there is provided a method of forming a balloon for a balloon catheter, including the steps of: providing a mold; providing one or more filar elements along the entire length of the mold; heating a balloon material in the mold; and inflating the balloon material to the shape of the mold to form the balloon, said balloon having a longitudinal direction; wherein the heating and inflating steps attach or embed the one or more filar elements on or in the balloon wall with the one or more elements extending solely in the longitudinal direction of the balloon.

Advantageously, the balloon material is formed by co-extruding raw material to form a balloon wall comprising an outer layer of a first material and an inner layer of a second material, wherein a softening or melting temperature of the first material is lower than a softening or melting temperature of the second material.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

It is to be understood that the drawings do not show the various elements of the device to scale and often these are shown in enlarged form, solely for the purposes of clarity of explanation.

Figure 1:
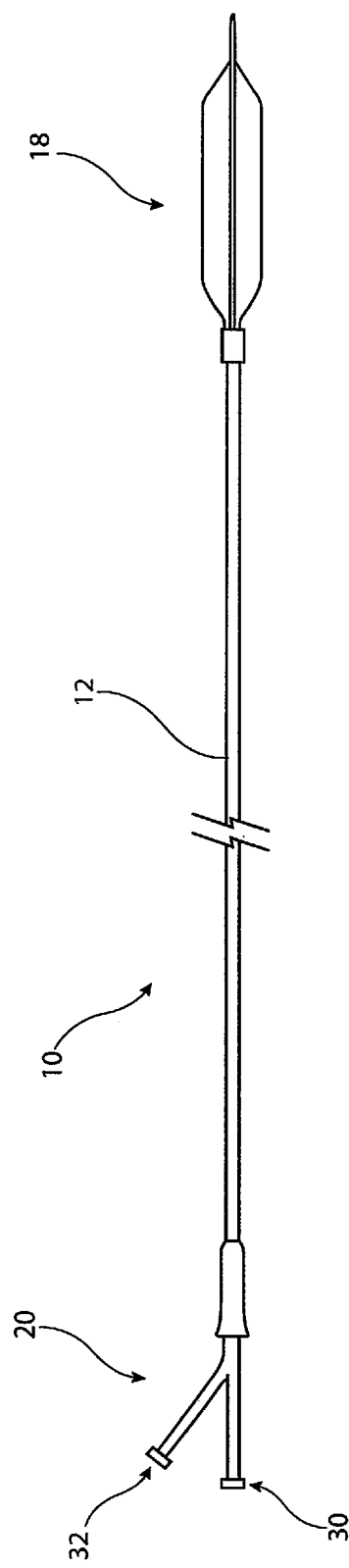
FIG. 1 shows a schematic view of an embodiment of balloon catheter introducer assembly.

Referring first to FIG. 1, there is shown an embodiment of introducer apparatus 10 which is deployed endoluminally in a patient and includes a catheter 12 on which a medical balloon 18 is fitted. The structures of the preferred embodiments of balloon are described in further detail below. The combination of catheter 12 and balloon 18 is typically termed a balloon catheter.

At a proximal end of the catheter 12 there is provided an external manipulation and valving unit 20. The unit 20 can be of conventional form and is therefore not described in detail herein as its components and structure will be readily apparent to the skilled person. Typically, the unit will include one or more ports 30, 32 for the supply or removal of fluid from the components of the apparatus 10, such as inflation fluid for the balloon 18 and flushing fluid into the assembly.

The balloon 18 is typically fitted into the introducer apparatus 10 in a deflated and wrapped condition, in which it has a small diameter, and is covered by a sheath (not shown). Upon location of the distal end of the assembly 10 at the site to be treated, the sheath is retracted to expose the balloon 18 and then the balloon 18 is inflated so as to adopt the shape shown for example in FIGS. 2 and 3.

Figure 2:
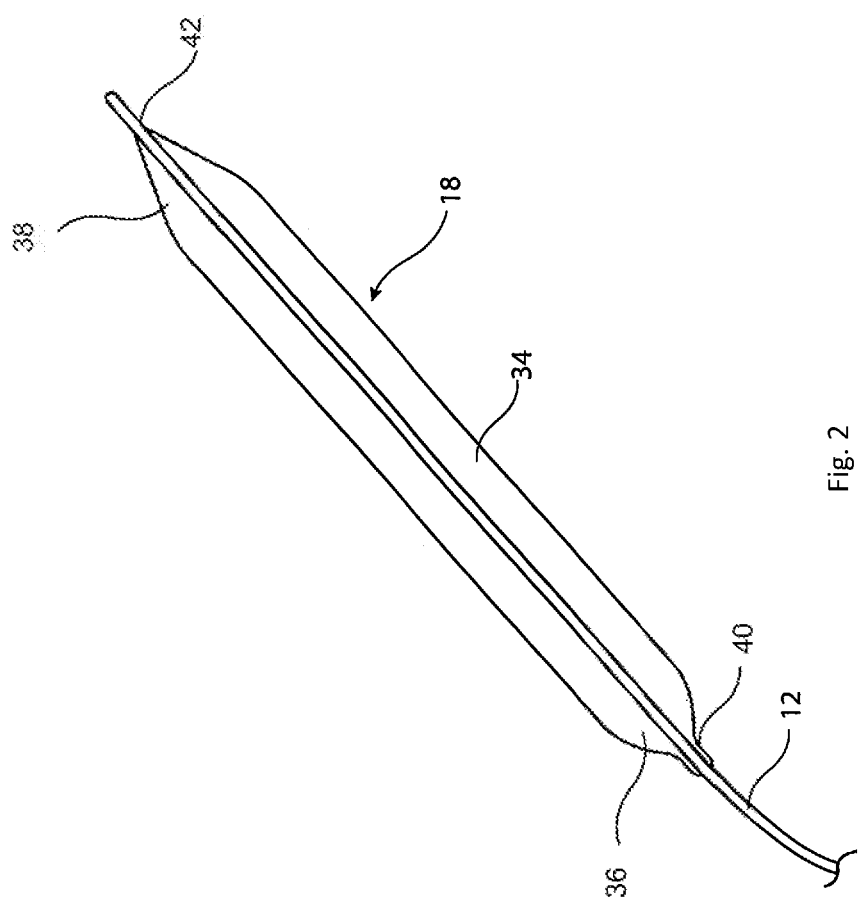
FIG. 2 is an enlarged cross-sectional view of the distal end of a balloon catheter of FIG. 1.

FIG. 2 shows an enlarged view of a typical balloon catheter and balloon 18 in longitudinal cross section. The balloon 18 normally has a generally circular cylindrical form and is secured at its ends to the catheter 12. The balloon 18 may be made of a thermoformable, substantially non-compliant material such as polyether block amide (such as Pebax), polyamide (such as Nylon 12), polyethylene, PET or polyurethane. The balloon may be formed from a co extrusion of different layers or blend of more than one of these materials.

As used herein, the term thermoformable refers in general to a material that may be shaped under conditions of temperature and/or pressure. Preferably, the thermoformable polymer is stretchable or formable, in some instances flowable, above a certain processing temperature, but takes a set form having desired resilience and strength properties at a temperature of intended use (such as room temperature to body temperature).

The balloon 18 is inflatable and thus impermeable or substantially impermeable, as well as being capable of being wrapped or folded to a relatively small diameter for endoluminal delivery.

When the balloon 18 is used to deploy a medical device, in practice the medical device is fitted over the balloon 18 when the latter is in a deflated and wrapped configuration on the catheter 12, in known manner.

In this embodiment, the balloon 18 has a substantially cylindrical body portion 34 and first and second end cones 36, 38 each bounded by a respective neck portion 40, 42. The portions 34 to 42 of the balloon 18 are typically formed by heating and inflation of a raw tubing in a suitable mold, as is described in more detail below. This heating and inflation forms the end cones 36, 38 as well as the body portion 34. Neck portions 40, 42 may be the unstretched raw tubing but may also be formed by radially compressing the end portions of the raw tubing during the heating and inflation process.

The balloon 18 is fixed or bonded to the catheter 12 at the neck portions 40, 42 of the balloon 18.

In general, it is preferred that the balloon 18 has relatively thin walls, as wall thickness affects the size (diameter) of the balloon when folded or wrapped as well as its flexibility. However, it is typical of prior art balloons that the end cones 36, 38 have walls which are thicker than the walls of the body portion 34 as a result of the balloon forming process. Specifically, the end cone portions 36, 38 will typically have a wall thickness which increases in the direction of narrowing of the taper, as a result of the lesser amount by which these portions expand during formation of the balloons.

Figure 3:
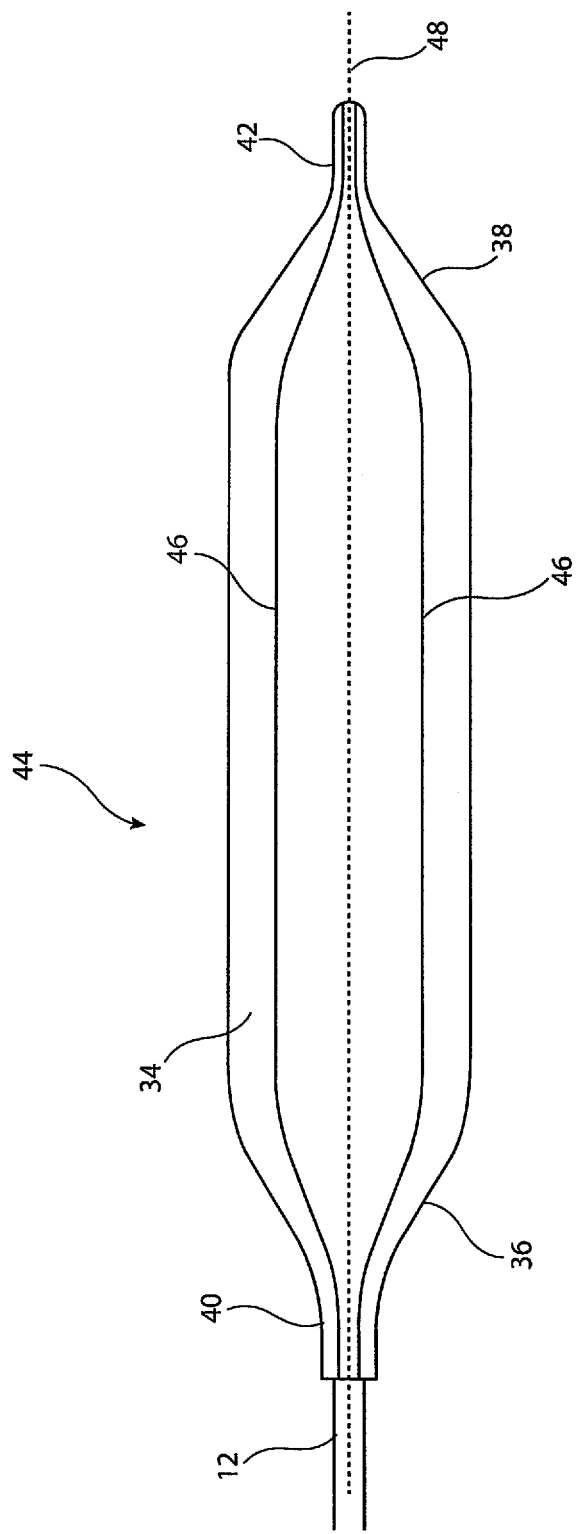
FIG. 3 is a side elevational view of a balloon structure in accordance with an embodiment of the present invention.

FIG. 3 shows a balloon 44 in accordance with an embodiment of the present invention. As with the balloon 18 shown in FIG. 2, the balloon 44 has in this example a cylindrical body portion 34 and first and second end cones 36, 38 each bounded by a respective neck portion 40, 42.

The wall of the balloon 44 may be a single layer or of a plurality of layers, preferably two layers of material which are coextruded and integral with one another. In the case that the balloon has two or more layers, the outer layer may be of a material having a softening or melting temperature which is lower than the softening or melting temperature of the material of the inner, underlying, layer. The wall of the balloon 44 could equally be formed of three of more layers. It is to be understood that the outer layer could be formed of a material which becomes more flowable than the inner layer of the balloon at the production temperatures used.

The thickness of the balloon wall is preferably between around 0.005 millimeters to around 0.08 millimeters, typically for a balloon having an inflated diameter of around 1.5 millimeters to around 36 millimeters.

The balloon 44 contains one of more filar elements 46, which are attached to or incorporated in the outer layer of the balloon structure 44. The purpose of the filar elements 46 is to halt the circumferential propagation of a tear in the balloon wall. These filar elements are strong but are thin and/or flexible so as not to affect adversely the properties of the balloon, in particular balloon flexibility and wrappability.

The balloon 44 of FIG. 3 has four sets of filar elements 46 extending along the length of the balloon, only two being visible in the view of FIG. 3. It is to be understood, though, that a different number of filar elements 46 may be used and in some instances there may be just a single filar element 46, while in other embodiments there may be two, three or more than four.

The filar elements 46 may be at least as flexible as the balloon wall and in some instances may be more flexible than the balloon wall. More particularly, the filar elements 46 may be at least as flexible as the balloon wall at least in a longitudinal direction of the balloon. In particular, the filar elements 46 are not intended to affect the normal characteristics or properties of the balloon 44, allowing the balloon to perform in the same manner as a balloon of similar structure but with no filar elements, especially to provide no scraping or scoring effect whatsoever to the balloon. In the preferred embodiment, the filar elements are compressible in a direction transverse to their length, having a hardness of no more than a hardness of the balloon wall, preferably less than that of the balloon wall.

Thus, in the preferred embodiment, the filar elements 46 do not materially affect the flexibility of the balloon. In practice, the filar elements 46 may be as flexible as the balloon wall at least in a longitudinal direction of the balloon. This leads to a structure in which circumferential propagation of a tear in the balloon wall is halted, without any compromise in the ability of the balloon to expand radially outwards, and without the need for an overly complex balloon structure or thickened balloon wall.

The at least one filar element 46 advantageously has a diameter of between around 0.01 millimeters and 0.05 millimeters.

The filar elements are formed of a material which is different from the material or materials of the balloon wall and could be formed as a single strand of material but in preferred embodiments are formed as a multi-stranded material. They may be made of natural or synthetic fiber or a combination of the two. Suitable materials include para-aramid synthetic fiber such as Kevlar, ultra high molecular weight polyethylene such as Dyneema, polytetrafluoroethylene fiber such as Gore-Tex, carbon fiber, cotton and the like. It is to be understood that the filar elements 46 may be made of a plurality or mix of these filar materials.

In the preferred embodiment, the filar elements have a linear density (dtex) of between 10 and 60 and are multi filamentary, each having from around 5 to 50 strands per element, most preferably around 25 strands. Each strand of the multi filament element may have a density of around 0.5 to 2 denier (or similar dtex density). The use of multi-filament elements provides a number of advantages. First, the elements are compressible in bulk, primarily by allowing sliding of the fibers or strands over one another, which results in increased compressibility. Secondly, the fibers can be made of a material of high tensile strength compared to the balloon yet without adversely affecting the longitudinal flexibility of the balloon.

Thirdly, the multi stranded filaments can minimize, particularly avoid, any surface differences or performance differences to the balloon compared to an equivalent balloon without such filar elements. Fourthly, these features allow for the use of materials which are significantly stronger than the balloon without affecting the performance characteristics of the balloon. Other advantages will become apparent to the skilled person.

The filar elements preferably have a tensile strength of between around 4 N to around 20 N. They may have an elongation at break of no more than around 5%. In other words, the filar elements have a substantial tensile strength with little elongation prior to breakage, which optimizes their qualities for stopping tear propagation.

Each filar element 46 extends longitudinally between the two ends of the balloon 44, preferably substantially parallel to the longitudinal axis 48 of the balloon structure 44. The filar elements 46 extend through the end cones 36, 38 and neck portions 40, 42, and extend all the way to the distal and proximal ends of the balloon 44. As such, the filar elements 46 act as strengthening elements for interconnecting the entire length of the balloon 44, that is to say filar elements 46 serve to connect both ends of the balloon 44 in a continuous manner such that all points along the length of the balloon 44 are attached to the filar element 46 at some location around the circumference of the balloon 44. In the preferred embodiment there are no filar elements 46 which extend circumferentially around the balloon 44, that is as annular rings around the balloon.

In the embodiment shown in FIG. 3, the filar elements 46 extend through the conical end portions and through the necks to the extremities of the balloon, that is for the entire extent of the balloon 44. It is not essential that the filar elements 46 extend all the way to the very extremities of the balloon. It is, however, important that the fibers extend from the body portion past the point where the balloon is fixed or bonded to the catheter and terminate in the region in which the balloon is fixed or bonded to the catheter. In the arrangement of FIG. 3, this means that the filar elements 46 may extend from the body portion 34 past the point where the end cones 36, 38 join the respective neck portions 40, 42, and terminate in the regions of the two neck portions 40, 42 but before the very ends of the balloon. For the sake of ease of manufacture, though, t is preferred that the filar elements extend for the entire length of the balloon.

Figure 4:
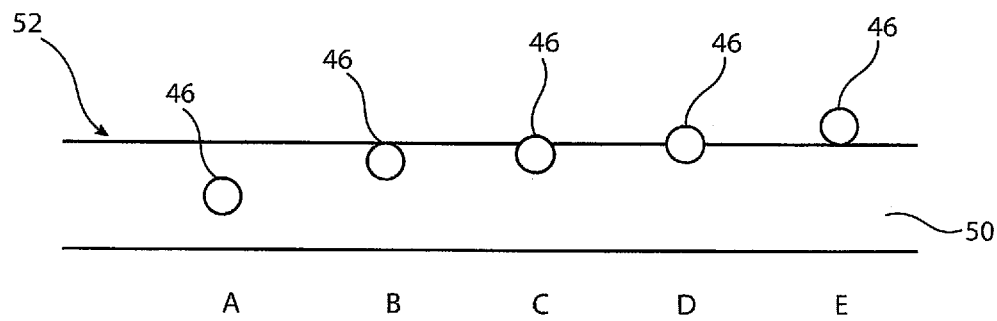
FIG. 4 is a schematic representation showing example positions of the fibers with respect to the balloon wall.

The filar elements 46 are preferably embedded in the balloon material, advantageously in an outer layer of the balloon. Various examples of the position of the filar elements 46 with respect to a balloon wall 50 are shown in FIG. 4. It is to be appreciated that in an embodiment the balloon has two layers and thus that FIG. 4 shows only the outer layer. In position "A", the filar elements 46 are completely embedded in the outer layer of the balloon wall 50, such that there is no protrusion from the outer surface 52 of the balloon. In position "B", the filar elements 46 are again completely embedded in the balloon wall 50 such that there is no protrusion from the outer surface 52 of the balloon, although the filar elements 46 are located proximate the outer surface 52 of the balloon. In position "C", the filar elements 46 are partially embedded in the balloon wall 50 such that a portion of each fiber 46 protrudes from the outer surface 52 of the balloon. In position "D", the filar elements 46 are partially embedded in the balloon wall 50 such that a portion of each filar elements 46 protrudes from the outer surface 52 of the balloon. The protruding portion of the filar elements 46 is greater in position "D" than in position "C". The filar elements 46 may even be positioned on the surface of the balloon 44, either on the outer surface or on the inner surface.

In the examples in which the filar elements protrude from the outer surface of the balloon, either the degree of this protrusion is small enough, or the filar elements are flexible enough, that their presence does not affect the function of the balloon. In the preferred embodiments, the filar elements have no noticeable or measurable effect on the characteristics of the balloon 44.

The materials of the filar elements 46, such as those disclosed herein, has a high tensile strength to as not to rupture should the balloon wall tear. Yet, they are sufficiently flexible not to materially affect the flexibility of the balloon. Moreover, by being attached to or embedded in the balloon wall, the filar elements 46 will wrap with the balloon for delivery and subsequent deployment. The nature of the filar elements will have no effect on the wrappability of the balloon.

The raw tubing used for the manufacture of the balloons taught herein is advantageously a continuous length of tubing having a substantially circular cylindrical tube portion.

Figure 5:
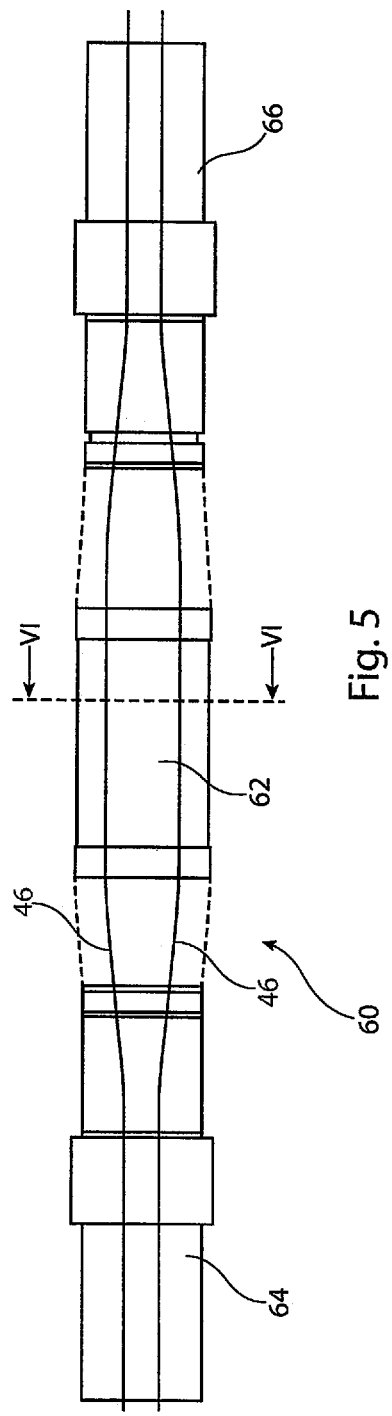
FIG. 5 is an exploded view of a mold in accordance with an embodiment of the present invention.
Figure 6:
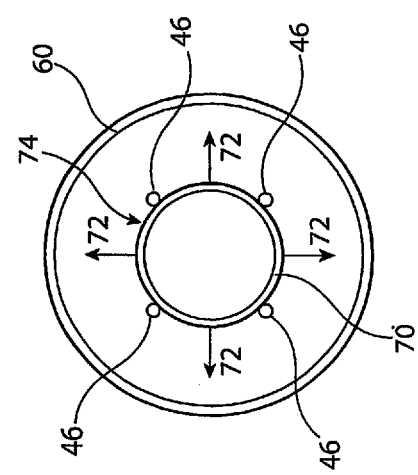
FIG. 6 is a cross-sectional view along line IV-IV of FIG. 5.

FIGS. 5 and 6 show an embodiment of apparatus used to mold such raw tubing into the required balloon form. As can be seen in FIG. 5, the mold 60 comprises a central body section 62 and two end caps 64, 66. The central body section 62 forms the body portion of the balloon, and the end caps 64, 66 form the respective end cones of the balloon. The end caps 64, 66, which may themselves be in a plurality of parts which can be disassembled, that is can be removed from the central section 62 for removal of the formed balloon from within the mold 60.

Prior to molding, one or more filar elements 46 are located through the mold 60, extending beyond the end caps 64, 66 of the mold 60. The raw tubing is fed into the mold from an end port and then inflated in the mold 60 under heat so as to stretch the central part of the raw tubing to form the body portion and end cones of the balloon, while the ends of the raw tubing are held radially compressed so as not to inflate, thus forming the neck portions of the balloon. After the balloon has been formed in this way, the balloon is cooled and then removed from the mold.

The inflation of raw tubing 70 in the mold 60 is shown diagrammatically in FIG. 6. The raw tubing 70 expands in the direction of the arrows 72 towards the inner surface of the mold 60, in so doing pushing the filar elements 46 towards the inner surface of the mold. When the raw tubing 70 is fully expanded with the filar elements 46 unable to move further, being bounded by the mold wall, they become at least partially embedded into the outer layer 74 of the balloon, which will have been heated at least to a softening or flowing temperature.

As described above, the preferred embodiment has a balloon formed of two layers, with the inner layer becoming less flowable than the outer layer during the balloon formation process. The filar elements 46 will therefore become embedded in the outer layer but not the inner layer of the balloon.

Subsequent cooling of the mold will cause cooling and then setting of the balloon, which can then be removed with the filar elements attached.

In FIG. 5 four filar elements 46 are located in the mold, and thus four filar elements 46 will extend generally linearly along the outer surface of the balloon. In practice, however, there may be provided a different number of filar elements 46 such as one, two, three or more than four.

Figure 7:
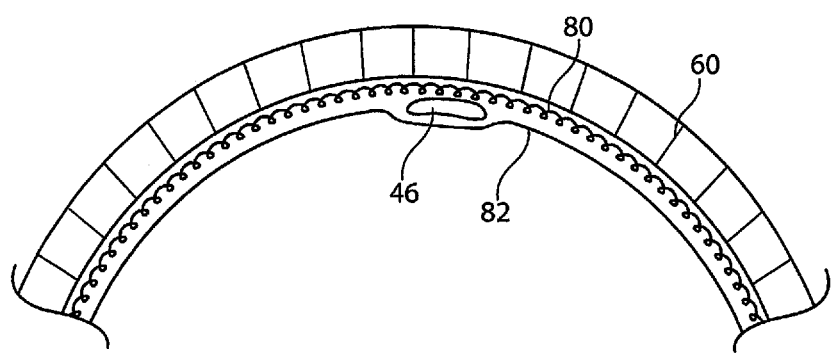
FIG. 7 shows a cross-section of a part of a balloon 44 in the process of manufacture.

Referring to FIG. 7, there is shown a cross-sectional schematic view of an example of mold with a balloon in the process of being formed. The mold has a mold wall 60 which supports the raw tubing on inflation, to the shape of the final balloon 44. In this embodiment the balloon 44 is formed of two layers, an outer layer 80 of a reflow material, or material with a lower softening temperature, and an inner layer 82 of a material having a higher softening temperature. The filar element 46 becomes embedded in the balloon, specifically within the outer layer 80. The inner layer 82 acts as a support layer, not only to the filar elements 46 but also to the outer player 80. Even though in the mild, the thickness of the filar elements 46 may cause the inner layer 82 to curve slightly around the filar elements 46, this will not be exhibited during later use of the balloon 44. As explained above, the filar elements 46 are flexible enough, and in some cases at least compressible enough, not to have any material effect on the characteristics or performance of the balloon 44.

In another embodiment, the balloon may be formed as a single layer, in which case the filar elements 46 will become embedded in the single layer of the balloon wall.

Other elements could be incorporated into the balloon structure in addition to the filar elements, depending on the intended purpose of the resulting balloon catheter. For example, one or more scoring elements could be disposed on the balloon.

Although the filar elements have been described as extending substantially linearly along the longitudinal direction of the balloon, this is not essential. They could extend at an angle thereto. They could, for example, wind around the balloon in a helical manner.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

What is claimed is:

1. A balloon catheter assembly, comprising:
    a catheter;
    an inflatable balloon having a longitudinal direction and comprising a balloon wall made from at least one balloon material and provided with a body portion, first and second end cones, and first and second neck portions, which neck portions are attached to the catheter, the balloon material having only two layers, an outer layer of a first material and an inner layer of a second material, wherein a softening or melting temperature of the first material is lower than a softening or melting temperature of the second material; and,
    one or more filar elements at least partially embedded in the outer layer but not the inner layer, wherein the one or more filar elements extend solely in the longitudinal direction of the balloon from the first neck portion to the second neck portion, and there are no filar elements that extend circumferentially around the balloon in an annular manner when the balloon is configured for delivery and subsequent deployment, and wherein the one or more filar elements are at least as flexible in a longitudinal direction as the balloon wall.

2. An assembly according to claim 1, wherein the one or more filar elements are at least as flexible as the balloon wall.

3. An assembly according to claim 1, wherein the one or more filar elements provide no material scoring or abrading function.

4. An assembly according to claim 1, wherein the one or more filar element or elements are compressible.

5. An assembly according to claim 1, wherein the balloon wall has a thickness of between about 0.005 millimeters and about 0.080 millimeters.

6. An assembly according to claim 1, wherein the one or more filar element has a diameter of between around 0.04 millimeters and 0.05 millimeters.

7. An assembly according to claim 1, wherein the one or more filar element has a linear density (dtex) of between 40 and 60.

8. An assembly according to claim 1, wherein the one or more filar element is multi-filamentary, each having from around 5 to 50 strands per element.

9. An assembly according to claim 8, wherein the one or more filar element has around 25 strands.

10. An assembly according to claim 8, wherein each strand has a density of around 0.5 to 2 denier.

11. An assembly according to claim 1, wherein the one or more filar element has a tensile strength of between around 4N to around 20N.

12. An assembly according to claim 1, wherein the one or more filar element exhibits an elongation at break of no more than around 5%.

13. An assembly according to claim 1, wherein the one or more filar element is at least one of: completely embedded in the balloon wall and partially embedded in the balloon wall.

14. An assembly according to claim 1, wherein the one or more filar material comprises natural and/or synthetic fiber.

15. An assembly according to claim 14, wherein the one or more filar material comprises as least one of: para-aramid synthetic fiber, ultra-high molecular weight polyethylene, polytetrafluoroethylene fiber, carbon fiber, and cotton.

* * * * *